United States Patent [19]

Sasmor

[11] 4,067,974

[45] Jan. 10, 1978

[54] STABILIZED SOLID FORM CHOLINE SALICYLATE COMPOSITIONS

[75] Inventor: Ernest J. Sasmor, Yonkers, N.Y.

[73] Assignee: The Purdue Frederick Company, Norwalk, Conn.

[21] Appl. No.: 705,056

[22] Filed: July 14, 1976

Related U.S. Application Data

[63] Continuation-in-part of Ser. No. 651,110, Jan. 21, 1976, abandoned.

[51] Int. Cl.² .................. A61K 31/60; A61K 31/615; A61K 31/61
[52] U.S. Cl. .................................. 424/231; 424/233; 424/234
[58] Field of Search ............... 424/233, 230, 234, 362, 424/231

[56] References Cited

U.S. PATENT DOCUMENTS

| | | | |
|---|---|---|---|
| 3,326,760 | 6/1967 | Halpern et al. | 424/230 |
| 3,347,744 | 10/1967 | Latshaw et al. | 424/362 |
| 3,759,980 | 9/1973 | Rosen et al. | 424/230 |

*Primary Examiner*—Sam Rosen
*Attorney, Agent, or Firm*—Harold D. Steinberg; Martin Blake; Alfred Halpern

[57] ABSTRACT

Choline salicylate is stabilized in solid form by means of a metal salicylate having a valence of at least 2, preferably aluminum, bismuth, calcium or magnesium salicylate. The composition is stabilized to a still greater degree by the addition thereto of carboxy-methyl cellulose. A still greater degree of stabilization is achieved by forming a complex of the choline salicylate, metal salicylate and carboxy-methyl cellulose. The complex is formed by preparing a solution of the carboxy-methyl cellulose, choline salicylate and metal salicylate, permitting complexng reaction to take place and drying. All of these stabilized forms of choline salicylate are used in solid dosage forms such as granules, tablets, capsules and supporitories for administration to animals and humans, in the course of choline salicylate therapy, to elevate the blood levels of salicylate ion.

20 Claims, No Drawings

STABILIZED SOLID FORM CHOLINE SALICYLATE COMPOSITIONS

CROSS REFERENCE TO RELATED APPLICATION

This is a continuation-in-part of my copending application Ser. No. 651,110, filed Jan. 21, 1976, entitled "Solid Choline Salicylate Compositions", now abandoned.

BACKGROUND OF THE INVENTION

Choline salicylate is a well known analgesic compound having desirable pharmacological and therapeutic properties, as described in U.S. pat. No. 3,069,321. The compound, however, possesses an inherent limitation of being highly hygroscopic so that it is not possible to prepare pharmaceutically acceptable, solid dosage forms which are useful for oral administration in the course of choline salicylate therapy of humans and animals. Although crystalline choline salicylate, melting at about 50° C., is known, its hydroscopic properties are such that trace amounts of moisture are sufficient to reduce the crystalline compound to the liquid state and no matter how stringent the effort to remove the absorbed moisture, the product remains in liquid state so that it cannot be used in forming stable solid dosage forms for pharmaceutical use.

Much effort has been made to prepare solid pharmaceutical dosage forms of choline salicylate. Thus, U.S. Pat. No. 3,297,529 provides mixtures of choline salicylate and magnesium sulfate to produce a solid product. U.S. Pat. No. 3,326,760 relates to the formation of an absorbate with polygalacturonic acid. U.S. Pat. No. 3,759,980 relates to the formation of a chemical compound of choline salicylate and magnesium salicylate, which is a solid. However, none of the methods described as solving the problem of providing choline salicylate in stable, solid, unit dosage-forms as described above, have as yet proved to be pharmaceutically satisfactory. A solid unit dosage form to provide a therapeutically sufficient quantity of choline salicylate for the required therapeutic purposes and also remain stable over sufficiently long periods of time to permit marketing of the same, has not been made commercially available, as yet.

SUMMARY OF THE INVENTION

Generally speaking, in accordance with the present invention choline salicylate is stabilized in solid form by admixture thereof with the salicylate salt of a metal having a valence of at least 2. The preferred metal salicylates are aluminum, bismuth, calcium and magnesium salicylate. The molar ratio of the choline salicylate to the metal salicylate is preferably between about 0.8:1 and about 1.2:1. Most preferably the choline salicylate and the metal salicylate are used in equimolar amounts.

According to a preferred embodiment of the present invention, carboxy-methyl cellulose is added to the mixture of the choline salicylate and the metal salicylate. It has been found that the addition of the carboxy-methyl cellulose has the effect of virtually doubling the shelf-life of the simple mixture. There is a wide range in the amount of carboxy-methyl cellulose that may be added to achieve the stabilizing effect. Preferably the amount of carboxy-methyl cellulose to be added is between about 2.5% by weight to about 25% by weight. The smaller amounts being preferred when low hydration levels of the mixture are present and to maximize the choline salicylate levels of the composition.

According to another embodiment of the present invention, a new complex compound is formed from choline, salicylic acid, metal ion and carboxy methyl cellulose. While this complex may contain wide proportions of its component moieties, choline salicylate, metal ion and carboxy methyl cellulose, its compositions is homogeneous, reproducible and constant, and it has been found to have a shelf-life in dry, solid form in excess of four years, which from the commercial standpoint may be considered as practically indefinite. Thus, the complexing of the choline salicylate with a metal ion and carboxy methyl cellulose results in the formation of an extremely stable, solid complex compound useful to prepare dsolid pharmaceutical dosage forms, which remains stable in excess of at least four years.

Furthermore, the complexed compounds formed between choline salicylate, carboxy methyl cellulose and metal ion, as for example, magnesium, aluminum, calcium and bismuth, may be distinguished from the solid compounds described in the prior art and also from the simple mixtures of its component moieties, on the basis of their chemical composition as well as their chemical, physical and pharmaceutical properties.

The difference among the separate compositions is apparent upon comparison of the critical solubility in polar solvents of magnesium-carboxy methyl cellulose-choline salicylate, the new complexed compound, with the simple mixture of choline salicylate and magnesium salicylate, with the simple mixture of choline salicylate, magnesium salicylate, and carboxy methyl cellulose, with the prior art chemical compound of U.S. Pat. No. 3,759,950, choline magnesium salicylate in polar solvents.

Electrical conductivity data determined for the compounds is in excellent agreement with the critical solubility data and establishes that the formed compound, magnesium-carboxymethylcellulose-choline salicylate, is materially different from the prior art formed compound magnesium choline salicylate in that it has a chelate intra-molecular structure in contrast to a hydrogen-bonded structure for the molecule of the prior art. Furthermore, the specific electrical conductivity of the formed, magnesiumcarboxymethylcellulose-choline salicylate, is distinguished from the simple mixture of its moieties, which in turn are distinguished from the formed hydrogen bonded compound of the prior art, magnesium choline salicylate.

The proportions of the choline salicylate, metal ion and carboxy methyl cellulose necessary to form the new complex compound of the present invention may vary within a wide range. Preferably the amount by weight of the carboxy methyl cellulose is between about 2.5% and about 25%. The amount of the choline salicylate is preferably between about 40% by weight and about 95% by weight. The amount of metal ion is preferably between about 2.5% and about 35% by weight.

While all of the compositions of the present invention, i.e. the mixture of choline salicylate and metal salicylate; the mixture of choline salicylate, a metal salicylate and carboxy methyl cellulose, and the new formed complex compounds of choline salicylate, metal ion and carboxy methyl cellulose, all provide stable, dry, free-flowing powders of choline salicylate, the new formed complexes provide the greatest degree of stability over the longest periods of time. In all cases the dried powders are useful to prepare pharmaceutically acceptable capsules, granules, tablets and suppositories by methods known in the art, and these new dry-solid powder compositions of choline salicylate may be used in any of these dosage-forms to treat humans and animals.

The new solid dosage forms prepared with either the simple mixtures, i.e., the mixture of choline salicylate and magnesium salicylate and the mixture of choline salicylate, magnesium salicylate and carboxy methyl cellulose or the formed compound choline salicylate-carboxy-methyl cellulosemetal ion complexes provide special advantages of convenience in administration of choline salicylate; an excellent physiologic tolerance, with virtual absence of side reactions and superior therapeutic efficacy evidenced by a rapid elevation of the salicylate ion level in the blood of humans and animals after the administration of tablets, capsules, granules or suppositories containing a therapeutically sufficient quantity of the appropriate choline salicylate-carboxy-methyl-cellulose-aluminum, bismuth, calcium or magnesium metal ion formed compound.

The simple mixture of choline salicylate and metal salicylate is obtained by mixing the component chemical compounds. However, since choline salicylate exists in dry state only for a short time when exposed to the atmosphere, the mixture is preferably obtained by first forming a concentrated solution of choline salicylate, adding the metal salicylate, i.e., magnesium salicylate, and then permitting the solvent to evaporate. The mixture with the carboxy methyl cellulose is prepared in the same way, e.g., either by dry mixing of ingredients or by formation of a solution of choline salicylate, dissolving the necessary ingredients therein and evaporating the solvent.

The new free-flowing choline salicylate complex compounds are prepared by first forming a solution of carboxy-methyl cellulose and then adding the choline component, the salicylic acid and the metal ion, as for example, aluminum, bismuth, calcium or magnesium ion. The formed metal carboxymethyl cellulose choline salicylate compound is allowed to set, whereupon it becomes thickened and then the mass dried, preferably at a temperature of about 40° C. The resultant dried powders comprising the formed complexed choline salicylate carboxy methyl cellulose metal compound analyze in good agreement for the theoretical quantities of choline salicylate, carboxy methyl cellulose, and the respective metallic ion.

The new powders, both the mixtures and the formed compound, retain their free-flowing solid characteristics for long periods of time without evidence of decomposition. Solid dosage forms, as for example, tablets, capsules, granules or suppositories, prepared with said solid powders are stable and also retain their potency overn an extended period of time.

When 10 gm. of either the aluminum, magnesium, bismuth or calcium carboxy methyl cellulose choline salicylate formed compound is placed in an open petri-dish and exposed to the atmosphere for extended periods, the powders remain in their original solid free-flowing stage, without decomposition. When formulated into solid pharmaceutically acceptable dosage forms which are packaged and stored at ambient room temperatures, these pharmaceutical preparations are stable for periods in excess of four years.

The preferred metallic ions to obtain the new powders are aluminum, bismuth, calcium and magnesium ions although other metal ions are useful. It should be noted that a valence of at least two is required for the metallic ion to enter into formation of the new solid free-flowing powders. Since the product is intended for therapeutic use, the suitability of the metallic ion is limited by its safety and activity. Thus, one would not utilize mercury or arsenic ions in this new process or such other metal ions which have inherent noxious properties affecting the safety of the patient, and these are also specifically excluded.

The general method used to form the new complexes of the present invention is illustrated in detail below.

It is well known that carboxy-methyl cellulose is insoluble in water in the dry acid form. It is necessary that the carboxy-methyl cellulose acid be converted into an aqueous solution and this may be accomplished by dissolving in water, the usual metallic salts of carboxy-methyl cellulose, as for example, sodium or potassium carboxy-methyl cellulose, in the desired concentration, and then removing the solubilizing ion, to wit, the sodium or potassium ion by means of an acid exchange column such as is well known in the art. The exact composition of the acid ion exchange column is not essential nor is it critical since any of the metallic ion exchange resins, as is used to remove sodium and potassium ions from a solution, is useful for this purpose. The ion exchange resins which are known in the art as sulfonated polystyrene polymers and which are cross-linked polyamine resins, are known in commerce by the trade name of "Amberlite" or more particularly as Amberlite IR or Amberlite IR-120 resins which are marketed by Rohm-Haas of Philadelphia, Pennsylvania. Resins of the same type are also marketed by other chemical concerns under different trade names which are well known in the art and some of these resins, together with the process for their preparation, are described in U.S. Pat. No. 2,402,384. These resins are used in the hydrogen form in the manner as is well known to the art in order to remove sodium and/or potassium ions.

By way of illustration, one gram molecular weight of choline bicarbonate is added to the prepared aqueous solution of carboxy-methyl cellulose obtained as the eluate from the acid ion exchange column after removal of the sodium or potassium ions, and the whole stirred while the mixture is warmed to about 70° C. The stirring is continued for about an hour or until there is no effervescence. The pH of the mixture is then determined and it will be within the range of pH 7 to pH 7.8 with an average pH value of pH 7.4.

Preferably three gram molecular weight of salicylic acid is then added to the choline bicarbonate-carboxy-methyl cellulose solution while stirring and the mixture is warmed maintaining the heat at about 55° C. for one hour. When all of the salicylic acid has been added and solution obtained, the mixture is allowed to return to room temperature and one gram molecular weight of the metal ion donor is added. The addition of the metallic ion donor compound is accomplished with strong stirring while the temperature is again increased to about 70° C. When all of the metal donor compound has been incorporated into the mixture and the solution is clear, stirring is stopped and the batch set aside to set overnight. After standing the mass becomes thick and the whole is then dried over about a 24 hour period in an oven set at 80° C. The resultant essentially dry material is pulverized and then dried further in the vacuum oven at a temperature of about 40° C. and 2 mm/Hg pressure, to constant weight. The dry powder thus obtained is the metal-choline salicylate-carboxy-methyl cellulose compound which is stable and possesses unique and reproducible properties useful to prepare solid dosage forms such as capsules, tablets, granules and suppositories which contain a therapeutically sufficient quantity of the above described active ingredient.

The metal ion donor compound described above provide a source of metal ion, and the following donor compounds are preferred for this purpose;

a. As a source of Aluminum ions: aluminum isopropoxide and aluminum hydroxide,
b. As a source of Magnesium ions: magnesium hydroxide and magnesium ethoxide,
c. As a source of Bismuth ions: bismuth citrate, bismuth phosphate or bismuth hydroxide,
d. As a source of Calcium ions: calcium hydroxide, calcium carbonate, calcium bicarbonate.

When choline salicylate is prepared in situ then choline chloride, choline carbonate or any other soluble salt of choline may be substituted at equivalent molecular quantity as is described above for choline bicarbonate. The new solid powders of choline salicylate may also be obtained when choline salicylate is added to the carboxy-methyl cellulose solution prior to the addition of the metal ion.

The dry powder of complex obtained through the present process are white, free-flowing and stable, having reproducible physical and chemical properties. The respective compounds (mol ratio of choline: salicylate: metal being 1:3:1) analyze as follows: aluminum choline salicylate carboxymethyl cellulose compound contains substantially 5.1 percent of aluminum ion; 91.65 percent of choline salicylate and 3.25 percent of carboxy-methyl cellulose; magnesium choline salicylate carboxy-methyl cellulose compound contains substantially magnesium ion, 3.0 percent, 92.3 percent of choline salicylate, 5.16 percent carboxy-methyl cellulose; calcium choline salicylate carboxy-methyl cellulose compound contains calcium 4.35 percent, choline salicylate 91 percent and carboxy-methyl cellulose 4.65 percent; and bismuth choline salicylate carboxy-methyl cellulose compound contains bismuth 27.28 percent, choline salicylate 49.5 percent and carboxymethyl cellulose 21.2 percent.

When it is desired to use the new complex compounds in the treatment of humans and animals to achieve an analgesic, antipyretic or anti-inflammatory effect, and to elevate the blood salicylate levels, then a therapeutically sufficient quantity of the appropriate new compound may be administered to humans and animals in the dosage form of a tablet, granule, capsule or suppository. While the preferred unit dosage concentration of the respective new dry choline salicylate carboxy-methyl cellulose metal ion complexes in the tablet, capsule, granule or suppository dosage form is a sufficient quantity of the respective formed compound to provide approximately 250 mg. of salicylate moiety per unit dose or about 339 mg. of aluminum choline salicylate carboxy-methyl cellulose compound; 370 mg. of magnesium choline salicylate carboxy-methyl cellulose compound; 395 mg. of calcium choline salicylate carboxy-methyl cellulose compound and 693 mg. of bismuth choline salicylate carboxy-methyl cellulose compound. The range in concentration per unit dose is from 0.1 Gm. of respective said active compound per unit dose to 1.0 Gm. of the selected active compound per unit dose. The exact dosage concentration required depends upon the therapeutic goal to be achieved and the needs of the individual patient.

The preparation of tablets is accomplished by mixing the appropriate quantity of the selected active ingredient, e.g. the mixture of choline salicylate and magnesium salicylate or the mixture of choline salicylate, magnesium salicylate and carboxy methyl cellulose or the complex of choline salicylate-metal ion-carboxy methyl cellulose, with a diluent, such as lactose, sucrose, starch, povidone or any other pharmaceutically acceptable tablet diluent and adding to this mixture a binder and a tablet lubricant, said binder and tablet lubricant being selected from the group of pharmaceutically accepted tablet binders and tablet lubricants as are well known in the art. The mixture is then granulated with ethyl alcohol and dried and the dried granular material is then compressed into pharmaceutical tablets of suitable size and shape.

An alternate tabletting procedure is to mix the appropriate quantity of the selected active ingredient described above with a pharmaceutically acceptable tablet diluent such as lactose, sucrose, starch or crystalline microcellulose, then, compressing the mixture into dry tablets in accord with the method known in the art as slugging, and then grinding the slugged tablet thus formed into a granular powder with a particle size not greater than No. 16 U.S. standard mesh size and then compressing said granular powder into pharmaceutically acceptable tablets of suitable size and shape.

Capsules are prepared by filling appropriate capsules with either the active ingredient alone, or mixed with a diluent. Such diluents as described above may be utilized for this purpose.

It may be desired to dispense the granules obtained from the tablet manufacturing procedure, but prior to compression into tablets, as a dispensing form in which case, the concentration of the selected active ingredient is adjusted on the basis of a 5 gram unit dose or such weight as would be conveniently dispensed in a standard unit dose.

Suppositories are prepared by mixing the selected active ingredient with an appropriate weight of cocoa butter or polyoxyethylene glycol having a molecular weight of greater than 1500 or in a compatible pharmaceutically acceptable suppository base. The suppositories are then shaped into the well known dosage form and dispensed in a unit weight so as to deliver the desired change.

When all of the above solid dosage forms containing the new compounds are used in therapy of humans and animals, they may be administered from one to six times daily in the dosage concentration sufficient to achieve the desired therapeutic daily dose.

DESCRIPTION OF PREFERRED EMBODIMENTS

The following examples are given to further illustrate the present invention. The scope of the invention is not, however, meant to be limited to the specific details of the examples.

EXAMPLE 1

In a suitable reaction flask, is placed a solution of 165 gms. of choline bicarbonate dissolved in 500 cc of water and to this is added 138 gms. of salicylic acid, in small increments, under constant stirring until the ebullition of carbon dioxide ceases. The solution of choline salicylate thus formed, is concentrated so that the concentration of choline salicylate is at least 90 percent by weight of the solution and there is no more than 10 percent of water present. To this solution is added 300 gms. of anhydrous magnesium salicylate, and the mixture stirred. A past-like mass soon forms which is then spread on a glass surface to dry. In a matter of a few hours a hard solid material is obtained which is pulverized to a fine powder and is useful for the preparation of tablets, capsules, granules and suppositories to provide choline salicylate in solid unit-dosage form.

The formed solid choline salicylate-containing material is a mixture that may be separated into component parts by treatment, for example, with water.

EXAMPLE 2

In place of the magnesium salicylate used as described in Example 1 above, there may be substituted in equimolar amounts, aluminum salicylate, aluminum hydroxy salicylate, bismuth salicylate and or calcium salicylate. It is important that the metallo salicylate salt used be anhydrous and substantially free of impurities. The resultant mixture is a free-flowing powder useful to prepare solid pharmaceutical dosage forms containing choline salicylate.

EXAMPLE 3

To an aqueous solution of choline salicylate containing at least 90 percent by weight of choline salicylate is added an equimolar proportion of anhydrous aluminum hydroxy salicylate under constant stirring, whereby a soft putty-like mass results. To this mixture, carboxymethyl cellulose is added from 2.5 percent to 25 percent by weight of the arithmetic sum of the weights of choline salicylate and aluminum hydroxy salicylate present in the soft mass, while the mixture is being milled. The soft mass hardens rapidly and may be pulverized to a fine powder. The resultant dry, solid mixture is a stable, dry free-flowing powder which is useful in the preparation of pharmaceutically acceptable solid dosage forms of choline salicylate.

In place of the aluminum hydroxy salicylate used above there may be substituted in equimolar proportions any one or a mixture of the following anhydrous metallic salts: aluminum salicylate, magnesium salicylate, bismuth salicylate and calcium salicylate, the remainder of the steps being the same.

In place of the carboxy methyl cellulose as used above, there may be substituted in equal parts by weight, carboxy-ethylcellulose or carboxy-propyl-cellulose or mixtures thereof, the remainder of the steps being the same.

While the preferred range in concentration of the amount of respective carboxy lower alkyl cellulose or mixtures thereof which are described above are from 2.5 percent to 25 percent by weight, an optimal range in weight of the cellulose component to be added is from 2.5 percent to 5 percent, by weight, with a preferred concentration range of between 3 percent and 4 percent by weight. The exact amount of carboxy alkyl (preferably methyl) cellulose to be added will depend upon the amount of water present in the mixture. Thus, when the concentration of water in the solution is 10 percent, or greater, by weight, then the upper range of between 15 percent and 25 percent by weight of carboxy alkyl cellulose will be used, but when the amount of water is between 10 percent and 15 percent by weight, then the weight of carboxy alkyl cellulose component to be added will be between 5 percent and 15 percent by weight, and when the amount of water is less than 10 percent by weight, then the range in the amount of carboxy alkyl cellulose used, will be between 2½ percent and 5 percent by weight.

EXAMPLE 4

Approximately 1 liter of a 4 percent solution of sodium carboxy methyl cellulose is cycled through a column containing an acidic ion exchange resin, as for example, Amberlite-IR-12OH, to remove the sodium ion from the solution. The eluate solution of carboxy methyl cellulose now contains approximately 75 percent by weight of solid matter and a sufficient quantity of said eluate to provide 33 gms. of carboxy methyl cellulose is mixed with an equimolar proportion of aluminum hydroxy salicylate and the mixture stirred, while warming. The water is removed under under vacuum distillation and the resultant dry solid material pulverized. The dry material contains the formed aluminum carboxy methyl cellulose disalicylate and may be used to form a stable, solid free-flowing powder of choline salicylate suitable for pharmaceutical use.

EXAMPLE 5

To an aqueous solution of choline salicylate containing 9 gm. of choline salicylate dissolved in 10 gm. of solution, is added an equimolar proportion of anhydrous aluminum carboxy methyl cellulose disalicylate whereupon a solid, past-like mass forms, which is then spread in thin-layers for air-drying. The resulting solid matter is then ground to a fine free-flowing powder which is stable and non-hygroscopic, and is useful to prepare pharmaceutically acceptable solid dosage forms containing choline salicylate as the active ingredient.

EXAMPLE 6

Approximately 4.5 liters of a 4 percent solution of sodium carboxy-methyl cellulose is cycled through a column containing an acidic ion exchange resin as for example, Amberlite-IR-120H to remove the sodium. The eluate solution of carboxy-methyl cellulose in water contains approximately 0.75 percent by weight of solid matter. A sufficient quantity of this eluate to provide 32.7 gm. of carboxy-methyl cellulose is placed in a glass flask fitted with a stirrer and a warming jacket. The carboxy-methyl cellulose solution is warmed to about 30° C. and 22.47 gm. of choline bicarbonate is added in small increments under rapid stirring. Vigorous ebulition occurs when the choline bicarbonate increments are added and the heat is increased slowly to 70° C. during the addition process. When all of the choline bicarbonate has been added, the mixture is stirred for approximately one hour while warming and then allowed to cool to room temperature. The pH of the solution is approximately pH 7.4 with a range of from pH 7.0 to pH 7.8. To this solution, at room temperature, is now added 48 Gms. of salicylic acid in divided increments under constant stirring. The mixture is heated for one hour and then the temperature raised to 70° C. and a sufficient quantity of aluminum isopropoxide to provide 2.9 Gm. of aluminum ion is added. The stirring and warming are continued for one hour; at the end of which time the batch is allowed to stand overnight.

The next day the thickened mass is spread out in a thin layer to dry under a hot oven at 80° C. When the material is dried, it is pulverized and then placed in a vacuum oven to continue the drying process at a temperature of 40° C., 29 inches of vacuum, until two successive samples show no further weight loss. The dried powder is then reground, packaged and filled into glass bottles. The formed compound is aluminum-choline-salicylate-carboxy-methyl-cellulose, a white powder containing 5.1 percent of aluminum, 91.65 percent of choline salicylate and 3.25 percent of carboxy-methyl cellulose. The powder is insoluble in water and stable on exposure to air at room temperature.

In place of the aluminum isopropoxide described as a source of the aluminum ion may be substituted aluminum-hydroxide dry gel or aluminum wet gel in a quantity sufficient to provide an equivalent amount of aluminum ion as set forth above.

EXAMPLE 7

To an aqueous solution of carboxy-methyl cellulose, 16.3 gm. of carboxy-methyl cellulose is added 166 gm. of choline bicarbonate. The mixture is stirred and warmed until the gas ebulition ceases and then 414.4 gm. of salicylic acid are added. The mixture is warmed and stirred until all of the solids have gone into solution. The stirring is continued while heating at 70° C. for about one hour and then 114.3 gm. of magnesium ethoxide are added. The mixture is stirred until all of the solid material enters into solution, the heating is continued for one hour and the mixture set aside overnight.

The next day the solution is dried to constant weight and the dry powder pulverized. The formed compound is magnesium-choline-salicylate-carboxy-methyl-cellulose which contains 2.5 percent of magnesium 92.3 percent of choline salicylate and 5.16 percent of carboxy-methyl cellulose. The dry white powder is insoluble in water and nonhygroscopic; is stable for prolonged periods of time when exposed to the atmosphere.

In place of the magnesium ethoxide used as a magnesium ion donor may be substituted 61.78 gm. of magnesium hydroxide.

EXAMPLE 8

To an aqueous solution of carboxy-methyl cellulose containing approximately 17 gm. of carboxy-methyl cellulose on an anhydrous basis is added one gram molecular weight of choline bicarbonate and 2 gm. molecular weight of salicylic acid. The mixture is stirred until complete solution is achieved and warmed to 70° C. while stirring and then 389 gm. of bismuth citrate is added, sufficient to provide approximately 1 gm. molecular weight of bismuth ion.

In place of bismuth citrate, any soluble bismuth salt may be used as for example, bismuth chloride or bismuth phosphate as the bismuth ion donor. When all of the bismuth compound has been added the mixture is stirred while heating until a clear solution results and then set aside overnight at room temperature. The material is then dried in vacuum to constant weight.

The dry white powder is bismuth-choline-salicylate-carboxy-methyl-cellulose which is stable at room temperature and is not hygroscopic. The compound analyzes in good agreement with the theoretical values.

EXAMPLE 9

To a solution of 4.6 gm. of carboxy-methyl cellulose diluent in 100 cc of water is added 91 gm. of choline salicylate dissolved in 100 cc of solution. The mixture is warmed to 70° C. for three hours, after which time 4.35 gm. of calcium ion obtained from calcium hydroxide or calcium bicarbonate is added. When all of the calcium salt is entered into solution, the mixture is set aside to stand for at least ten hours and then the product dried in vacuum to constant weight. The resultant formed white powder is calcium-choline-salicylate-carboxy-methyl cellulose, a stable, nonhygroscopic powder analyzing in good agreement with its theoretical values.

EXAMPLE 10

When 19 gm. of either aluminum-choline-salicylate-carboxy-methyl-cellulose, magnesium-choline-salicylate-carboxy-methyl-cellulose, bismuth-choline-salicylate-carboxy-methyl-cellulose, or calcium-choline-salicylate carboxy-methyl-cellulose are extracted with chloroform and the solvent evaporated the residue is not more than 10 mg. This test establishes that there is no separation of the salicylic acid from the respective formed compound, obtained as a result of Examples 6 through 9 described above.

A 10 gm. sample of the choline salicylate carboxy-methyl cellulose metal compound, obtained as a result of Examples 6 through 9 above is placed on a tared petri dish which is then exposed to the atmosphere on an open shelf. An equal quantity of crystalline choline salicylate, melting at about 50° C. which is prepared in accord with the method described in U.S. Pat. No. 3,069,321 is then placed on another petri-dish placed side-by-side to the petri dish containing the formed choline salicylate carboxy-methyl cellulose metal compound prepared as described in Examples 6 through 9 above. Both petri dishes are examined at hourly intervals for the first day and at 8-hour intervals thereafter. At each observation point, each petri dish is weighed to determine any increase in weight due to absorption of water and the physical state of the solid material is evaluated to determine whether any changes occurred in the respective compounds. After one hour of atmospheric exposure, the crystalline choline salicylate compound, prepared in accord with U.S. Pat. No. 3,069,321, liquified while the formed new compounds prepared in accord with the method described in Examples 6 through 9, remain in their original solid state. The liquified choline salicylate showed an increase in weight of 1,963 mg. which indicates an absorption of water of almost 20 percent whereas the formed new compounds showed an increase in weight of only 67 mg. which indicates that there was virtually no hygroscopic activity.

After three days of exposure to the atmosphere on the open shelf, the liquified choline salicylate compound absorbed about 40 percent by weight (4.136 gm.) of water whereas the formed new compounds showed an increase in weight of less than one percent or 331 mg. The free-flowing powder characteristics of the formed new compounds remained unchanged throughout the test period. This test establishes that complexing of the moieties occurs which modifies the ability of choline salicylate to absorb water from the atmosphere. It is known that hydrogen bonding does occur between choline salicylate and water and the effect of the said new compounds is to preferentially block the site of hydrogen bonding to prevent the absorption of water molecules by the hygroscopic compound.

When an equal quantity of the solid choline salicylate composition comprising a mixture of choline salicylate and magnesium salicylate is placed in a tared petri dish and exposed to the atmosphere at room temperature, the perti dish is examined at hourly intervals the first day and at 8 hour intervals thereafter. There is an increase in weight about 8.7% after 3 days of exposure to the atmosphere. When this test is repeated with the solid composition obtained by mixing choline salicylate, magnesium salicylate and carboxy methyl cellulose, after 3 days of exposure to the atmosphere in an open petri dish there is a gain in weight 4.2%.

In all of the tests conducted with the solid choline salicylate compositions described above, the free flowing powder characteristics were not modified by atmospheric exposure for 3 days.

EXAMPLE 11

The ability of the solid choline salicylate compositions obtained as a result of Examples 1 through 9 above to retain their solid state characteristics was evaluated by exposing a 2 gm. sample of the respective composition and was placed in a tared glass dish and stored under different humid atmospheric conditions up to 97% relative humidity at the elevated controlled temperature of 37° C. At predetermined intervals the samples were examined and the physical state of the exposed powder recorded.

Choline salicylate, melting at 49.3°, prepared according to U.S. Pat. No. 3,069,321, liquidfied within 2 minutes exposure at all relative humidities studied.

Magnesium choline salicylate, prepared in accord with U.S. Pat. No. 3,759,980, liquified after 32 hours of exposure to an atmosphere of 60% relative humidity at 37° C, 20 hours of exposure to an atmosphere of 80% relative humidity at 37° C and 18 hours of exposure to an atmosphere of 90% relative humidity at 37° C.

Magnesium-carboxy methyl cellulose-choline salicylate obtained as a result of Example 7 remained solid when exposed for seven days to an atmosphere of 90% relative humidity at 37° C, but liquified after seven days exposure to an atmosphere of 97% relative humidity at 37° C.

Aluminum carboxy methyl cellulose choline salicylate obtained as a result of Example 6 was partially solid after seven days exposure to 80% relative humidity at 37° C and also after seven days exposure to an atmosphere of 90% relative humidity at 37° C.

Calcium carboxy methyl cellulose choline salicylate obtained as a result of Example 9 liquified after seven days of exposure to an atmosphere of 60% relative humidity and and greater relative humidities at 37° C.

The mixture of choline salicylate and magnesium salicylate, obtained as a result of Examples 1 – 4 liquified after 30 hours of exposure to an atmosphere of 60% relative humidity at 37° C; 24 hours of exposure to an atmosphere of 80% relative humidity at 37° C; and 20 hours of exposure to an atmosphere of 90% relative humidity.

The mixture of magnesium salicylate, choline salicylate and carboxy methyl cellulose, obtained as a result of Example 3 above liquified after 4 days exposure to an atmosphere of 60% relative humidity at 37° C; after 3 days of exposure to an atmosphere of 80% relative humidity at 37° C, and about 2.5 days exposure to an atmosphere of 90% relative humidity at 37° C.

The mixture of aluminum salicylate and choline salicylate obtained as a result of Example 2 liquified after 4 days of exposure to an atmosphere of 80% relative humidity at 37° C and after approximately 3 days (3.2 days) atmosphere of 90% relative humidity at 37° C.

The mixture of aluminum salicylate, choline salicylate and carboxy methyl cellulose obtained as a result of Example 3 above, liquified after approximately 4 days (4.3 days) of exposure to an atmosphere of 80% relative humidity at 37° C and after 3.5 days of exposure to an atmosphere of 90% relative humidity at 37° C.

EXAMPLE 12

Measured portions of the mixtures or compounds obtained as a result of Examples 1 through 9 above are compressed into tablets utilizing conventional tableting procedures and inert tablet excipients so as to provide tablets containing dosage units of about 435 mg. of choline salicylate which is the approximate equivalent with respect to salicylic acid content of the conventional 5 grain of aspirin tablet.

EXAMPLE 13

A suitable measured quantity of the formed mixtures or compounds obtained as a result of Examples 1 through 9 above are filled into gelatin capsules of suitable size and shape to provide a unit dose of at least 435 mg. of choline salicylate which is the approximate equivalent in salicylic acid content to a 325 mg. aspirin tablet. Suitable inert pharmacentucally acceptable and compatible capsule excipients may be used if necessary.

EXAMPLE 14

A measured portion of choline salicylate of the respective solid metal choline salicylate carboxy-methyl cellulose compound obtained as a result of Examples 6 through 9 above, sufficient to provide 435 mg. of choline salicylate per unit dose is mixed with a sufficient quantity of a pharmaceutically acceptable suppository dose carrier as for example, polyoxyethylene glycol with a molecular weight greater than 1500 and the mixture shaped into suppositories of suitable size and shape so that each suppository contains 558 mg of choline salicylate per suppository.

EXAMPLE 15

A suitable quantity of the respective metal choline salicylate carboxy-methyl cellulose compound obtained as a result of Examples 6 through 9 above is mixed with a quantity of a pharmaceutically acceptable diluent so that a mixture sufficient to provide 435 mg. of choline salicylate for 5 gm. of the mixture is obtained. The mixture is granulated with ethanol and passed through a No. 16 granulating screen and dried.

Any of the mixtures or complexes of the present invention may be used to elevate the blood salicylate ion concentration by administration of such mixture or complex in any form whatsoever. These mixtures and complexes, however, provide the advantage of administration in solid dosage form, e.g. in the form of granules, tablets, capsules or suppositories.

Throughout the specification, in disucssion of both the compositions or mixtures and the complexes, reference has been had mainly with respect to carboxy methyl cellulose. It should be understood, however, that any carboxy lower alkyl cellulose can be used such as carboxy ethyl cellulose, carboxy propyl cellulose, etc. Carboxy methyl cellulose is most preferred from the standpoint of availability and economy.

What is claimed is:

1. Solid composition comprising choline salicylate and a stabilizing amount of the salicylate of at least one physiologically compatible metal having a valence of at least 2.

2. Composition according to claim 1 wherein said metal is selected from the group consisting of aluminum, bismuth, calcium and magnesium.

3. Composition according to claim 1 wherein said metal is magnesium.

4. Composition according to claim 1 wherein the mol ratio of said choline salicylate to said metal salicylate is between about 0.8:1 and 1.2:1.

5. Composition according to claim 1 and also including a carboxy lower alkyl cellulose.

6. Composition according to claim 5 wherein said carboxy lower alkyl cellulose is carboxy methyl cellulose.

7. Composition according to claim 5 wherein said carboxy lower alkyl cellulose is present in an amount of about 2.5 – 40% by weight.

8. Composition according to claim 4 and also including a carboxy lower alkyl cellulose in an amount of about 2.5 – 25% by weight.

9. Solid pharmaceutical unit dosage form for choline salicylate therapy for administration to humans and animals, comprising an effective amount of the composition of claim 1 and a solid pharmaceutically acceptable carrier therefor.

10. Solid pharmaceutical unit dosage form for choline salicylate therapy for administration to humans and animals, comprising an effective amount of the composition of claim 5 and a solid pharmaceutically acceptable carrier therefor.

11. Method of elevating blood salicylate ion concentration in a human or animal, which comprises administering to said human or animal a therapeutically effective quantity of the composition of claim 1.

12. Method of elevating blood salicylate ion concentration in a human or animal, which comprises administering to said human or animal a therapeutically effective quantity of the composition of claim 5.

13. Choline salicylate-carboxy lower alkyl cellulose-metal complex wherein said metal is a physiologically compatible metal having a valence of at least 2.

14. Complex according to claim 13 wherein said metal is selected from the group consisting of aluminum, bismuth, calcium and magnesium.

15. Complex according to claim 13 wherein said metal is magnesium.

16. Complex according to claim 13 wherein said choline salicylate is in an amount of about 40-95% by weight, said carboxy lower alkyl cellulose is in an amount of about 2.5-25% by weight and said metal ion is in an amount of about 2.5-35% by weight.

17. Method of producing the complex of claim 13, which comprises forming an aqueous solution of a carboxy lower alkyl cellulose and choline salicylate, adding a source of a physiologically compatible metal ion having a valence of at least 2 to said solution in an amount sufficient to complex with said choline salicylate and said carboxy lower alkyl cellulose, permitting the resulting reaction mass to stand until it thickens and drying the thus thickened reaction mass, thereby obtaining a dry material consisting essentially of the complex of claim 13.

18. Method according to claim 17 wherein said metal ion source is selected from the group consisting of aluminum isopropoxide, aluminum hydroxide, bismuth citrate, bismuth phosphate, bismuth hydroxide, calcium hydroxide, calcium carbonate, calcium bicarbonate, magnesium hydroxide and magnesium ethoxide.

19. Solid pharmaceutical unit dosage form for choline salicylate therapy for administration to humans and animals, comprising an effective amount of the complex of claim 13 and a solid pharmaceutically acceptable carrier therefor.

20. Method of elevating blood salicylate ion concentration in a human or animal, which comprises administering to said human or animal a therapeutically effective quantity of the complex of claim 13.

* * * * *